(12) United States Patent
Vinci

(10) Patent No.: US 10,357,600 B2
(45) Date of Patent: Jul. 23, 2019

(54) EXTRACORPOREAL BLOOD TREATMENT SYSTEM, DISPOSABLE SET AND VALVE UNIT FOR PRE/POST INFUSION

(71) Applicant: GAMBRO LUNDIA AB, Lund (SE)

(72) Inventor: Luca Vinci, Poggio Rusco (IT)

(73) Assignee: Gambro Lundia AB, Lund (SE)

( * ) Notice: Subject to any disclaimer, the term of this patent is extended or adjusted under 35 U.S.C. 154(b) by 268 days.

(21) Appl. No.: 15/102,998

(22) PCT Filed: Oct. 9, 2014

(86) PCT No.: PCT/EP2014/071639
§ 371 (c)(1),
(2) Date: Jun. 9, 2016

(87) PCT Pub. No.: WO2015/086189
PCT Pub. Date: Jun. 18, 2015

(65) Prior Publication Data
US 2016/0310656 A1    Oct. 27, 2016

(30) Foreign Application Priority Data

Dec. 11, 2013 (EP) .................................... 13196628

(51) Int. Cl.
*A61M 1/34* (2006.01)
*A61M 1/36* (2006.01)
*A61M 39/24* (2006.01)

(52) U.S. Cl.
CPC .......... *A61M 1/3434* (2014.02); *A61M 1/342* (2013.01); *A61M 1/3627* (2013.01);
(Continued)

(58) Field of Classification Search
CPC .. A61M 1/342; A61M 1/3434; A61M 1/3627; A61M 2039/2453;
(Continued)

(56) References Cited

U.S. PATENT DOCUMENTS 4,683,916 A   8/1987   Raines
4,702,829 A   10/1987  Polaschegg
(Continued)

FOREIGN PATENT DOCUMENTS

AU   2013206508   1/2014
CA   2606540      12/2005
(Continued)

OTHER PUBLICATIONS

PCT Search Report and Written Opinion for Application No. PCT/EP2014/071639 dated Jun. 1, 2015 (12 pages).

*Primary Examiner* — Terry K Cecil
(74) *Attorney, Agent, or Firm* — Mueting, Raasch & Gebhardt, P.A.

(57) ABSTRACT

Disposable set for an extracorporeal blood treatment system. The disposable set includes an extracorporeal blood circuit having a blood withdrawal line and a blood return line configured to be attached to a blood treatment device and an infusion circuit coupled to the extracorporeal blood circuit through infusion lines. The disposable set further includes an infusion valve unit configured to be releasably connected to an infusion pump of the extracorporeal blood treatment system, the infusion valve unit incorporating a one-way valve or seal to control the flow of infusion liquid through the infusion cicuit.

32 Claims, 6 Drawing Sheets

(52) U.S. Cl.
CPC ..... *A61M 39/24* (2013.01); *A61M 2039/2453* (2013.01); *A61M 2039/2466* (2013.01); *A61M 2205/11* (2013.01); *A61M 2205/121* (2013.01); *A61M 2205/128* (2013.01); *A61M 2205/50* (2013.01); *A61M 2205/52* (2013.01)

(58) Field of Classification Search
CPC ...... A61M 2039/2466; A61M 2205/11; A61M 2205/121; A61M 2205/128; A61M 2205/50; A61M 2205/52; A61M 39/24
See application file for complete search history.

(56) References Cited

U.S. PATENT DOCUMENTS

| | | | |
|---|---|---|---|
| 4,919,167 | A | 4/1990 | Manska |
| 5,771,935 | A | 6/1998 | Myers |
| 5,935,100 | A | 8/1999 | Myers |
| 6,290,682 | B1 | 9/2001 | Myers |
| 9,134,282 | B2 | 9/2015 | Frej |
| 2006/0089605 | A1 | 4/2006 | Fitzgerald |
| 2009/0084720 | A1* | 4/2009 | Dannenmaier ......... A61M 1/16 210/188 |
| 2010/0274168 | A1 | 10/2010 | Gronau |
| 2011/0046535 | A1 | 2/2011 | Jonsson |
| 2013/0028788 | A1 | 1/2013 | Gronau |
| 2014/0038083 | A1 | 2/2014 | Sasaki |
| 2014/0299212 | A1 | 10/2014 | Colm |

FOREIGN PATENT DOCUMENTS

| | | |
|---|---|---|
| CA | 2238118 | 1/2006 |
| CA | 2654090 | 12/2007 |
| CN | 01052428 | 10/2007 |
| CN | 102006896 | 4/2008 |
| CN | 101986776 | 3/2011 |
| CN | 102077088 | 5/2011 |
| CN | 102438676 | 5/2012 |
| EP | 0189561 | 7/1990 |
| EP | 0634181 | 1/1995 |
| EP | 0711570 | 5/1996 |
| EP | 0562246 | 4/2000 |
| EP | 1099457 | 5/2001 |
| EP | 1424089 | 8/2011 |
| GB | 2029936 | 3/1980 |
| JP | 2013169373 | 9/2013 |
| WO | WO 93/01859 | 2/1993 |
| WO | WO 95/15194 | 6/1995 |
| WO | WO 97/47339 | 12/1997 |
| WO | WO 2007/104334 | 9/2007 |
| WO | WO 2008/050126 | 5/2008 |
| WO | WO 2008/146144 | 12/2008 |
| WO | WO 2009/051669 | 4/2009 |
| WO | WO 2009/074588 | 6/2009 |
| WO | WO 2010/121819 | 10/2010 |
| WO | WO 2013/147697 | 10/2013 |

* cited by examiner

EXTRACORPOREAL BLOOD TREATMENT SYSTEM, DISPOSABLE SET AND VALVE UNIT FOR PRE/POST INFUSION

This application is a U.S. National Stage Application of International Application No. PCT/EP2014/071639 filed Oct. 9, 2014, which was published in English on Jun. 18, 2015, as International Patent Publication WO 2015/086189 A1. International Application No. PCT/EP2014/071639 claims priority to European Application No. 13196628.5 filed Dec. 11, 2013.

The technology described herein relates generally to treating blood outside (i.e., extracorporeal) of a patient's body. More specifically, the technology relates to an extracorporeal blood treatment system with a valve unit for pre- and/or post-infusion of a predetermined fluid to the patient's blood.

An extracorporeal blood treatment involves removing blood from a patient, treating the blood outside the patient's body, and returning the treated blood to the patient. Extracorporeal blood treatment may be used to extract undesirable substances or molecules from the patient's blood, and, if necessary, to add desirable substances or molecules to the blood. An extracorporeal treatment of blood may be required, for example, when a patient's kidneys are unable—whether temporarily or permanently—to effectively remove substances from the blood. The patient is then required to undergo extracorporeal blood treatment to add or remove substances to the blood, to maintain a certain acid/base balance or to remove excess body fluids, for example.

This is typically accomplished by passing blood through a treatment unit, e.g., a dialyzer or a hemofilter. Blood is removed from the patient in, e.g., a continuous flow, and introduced into a primary chamber, also referred to as blood chamber, of the treatment unit. Therein, the blood flows past a semipermeable membrane that selectively allows matter in the blood to cross the membrane from the primary chamber into a secondary chamber and also selectively allows matter in the secondary chamber to cross the membrane into the blood in the primary chamber, depending on the type of treatment. The secondary chamber is also referred to as fluid chamber.

A number of different types of extracorporeal blood treatments may be performed. In an ultrafiltration (UF) treatment, undesirable matter is removed from the blood by convection across a membrane into the secondary chamber. In a hemofiltration (HF) treatment, the blood flows past the semipermeable membrane as in a UF treatment and desirable matter is added to the blood, typically by dispensing a fluid into the blood either before and/or after it passes through the treatment unit and before it is returned to the patient. In a hemodialysis (HD) treatment, a secondary fluid containing desirable matter is introduced into the secondary chamber of the treatment unit. Undesirable matter from the blood crosses the semipermeable membrane into the secondary fluid and desirable matter from the secondary fluid may cross the membrane into the blood. In a hemodiafiltration (HDF) treatment, blood and secondary fluid exchange matter as in HD, and, in addition, matter is added to the blood, typically by dispensing a fluid into the treated blood before its return to the patient as in HF.

As mentioned, in some of these treatments, fluid and with it predetermined matter can be added to the patient's blood. In these cases, if some of the removed fluid needs to be replaced, a correctly balanced electrolyte/buffer dialysis solution (also named infusion fluid or replacement fluid) is infused into the extracorporeal blood circuit. With reference to the blood flow, this infusion may be done either before the dialyzer (pre-infusion) or after the dialyzer (post-infusion), or both. Pre-infusion and post-infusion are also referred to as pre-dilution and post-dilution, respectively, as any infusion of liquid leads to a dilution of the blood.

EP 1424089 discloses a dialysis machine having an infusion main tube that forks into a pre-dilution tube and a post-dilution tube, wherein the main tube is coupled to an infusion pump. A valve set is arranged downstream from the fork to act upon the pre- and post-dilution tubes. The valve set includes a pinch valve and an electromagnet for operating the valve. A control unit operates the pinch valve to control the flow of the infusion liquid in the pre- and post-dilution tubes.

Although EP 1424089 focuses on controlling the infusion flow using the valve set, in systems for extracorporeal blood treatment other aspects need to be addressed as well to ensure a safe and reliable treatment of the patients. These aspects concern, for example, the ease of handling disposables such as circuits for blood and dialysis fluid to reduce the time for setting up the system and the risk of misconnections. Another aspect concerns the risk of cross-contaminating non-disposable components of the system with fluids (e.g., blood) from a patient.

There is, therefore, a need for an improved technology for an extracorporeal blood treatment system, in particular with respect setting up the system and protecting the system from cross-contamination.

Accordingly, a $1^{st}$ aspect relates to an extracorporeal blood treatment system having a first holder, a second holder, an infusion pump and an infusion valve unit. The first holder is mounted on a housing of the system and configured to hold a blood treatment device having a blood chamber, a fluid chamber and a semipermeable membrane that separates the chambers from each other. The second holder is mounted on the housing and configured to hold an extracorporeal blood circuit coupled to the blood treatment device. The infusion valve unit has a first part and a second part releasable connectable to the first part. The first part is mounted on the housing, and has an inlet coupled to the infusion pump. The second part has a first outlet and a second outlet that are connected to an infusion circuit configured to couple to the extracorporeal blood circuit. Further, the second part has a one-way valve configured to allow infusion liquid to flow from the inlet towards at least one of the first and second outlets, and to block fluid flow towards the inlet.

A $2^{nd}$ aspect involves a valve unit for an extracorporeal blood treatment system. The valve unit has a first part, a second part and a one-way valve positioned in the second part. The first part is configured to be mounted on a housing of the extracorporeal blood treatment system, and having an inlet configured to couple to an infusion pump. The second part is configured to be releasable connectable to the first part, and has a first outlet and a second outlet, wherein each outlet is configured to connect to an infusion circuit configured to couple to an extracorporeal blood circuit. The one-way valve is configured to allow infusion liquid to flow from the inlet towards at least one of the first and second outlets, and to block fluid flow towards the inlet.

A $3^{rd}$ aspect involves a disposable set for an extracorporeal blood treatment system. The disposable set comprises an extracorporeal blood circuit comprising a blood withdrawal line and a blood return line configured to be coupled to a blood treatment device. The disposable set comprises an infusion circuit comprising infusion lines coupled to the extracorporeal blood circuit. The disposable set comprises at least a part of an infusion valve unit. Said at least a part comprises a first outlet and a second outlet connected to the infusion lines. Said at least a part comprises a one-way valve configured to allow infusion liquid to flow from an inlet towards at least one of the first and second outlets and to block fluid flow towards the inlet. Said at least a part is configured to be releasably connectable to an infusion pump of the extracorporeal blood treatment system.

Further aspects of the invention are illustrated in the following.

In a $4^{th}$ aspect according to the $3^{rd}$ aspect, said at least a part is a second part of the infusion valve unit, wherein said second part comprises the first outlet and the second outlet and is configured to be releasably connectable to a first part of said valve unit, wherein said first part comprises the inlet and is mounted on a housing of the extracorporeal blood treatment system and connected to the infusion pump.

In a $5^{th}$ aspect according to the $3^{rd}$ aspect, said at least a part comprises all the infusion valve unit, provided with the inlet and the first and second outlet, and a connector coupled to the inlet and configured to be releasably connectable to a connector mounted on a housing of the extracorporeal blood treatment system and connected to the infusion pump.

In a $6^{th}$ aspect according to at least one of the previous aspects, the infusion lines comprise a pre-infusion line and a post-infusion line.

In a $7^{th}$ aspect according to at least one of the previous aspects, a pre-infusion line connects the infusion valve unit to the blood withdrawal line of the extracorporeal blood circuit and a post-infusion line connects the infusion valve unit to the blood return line of the extracorporeal blood circuit.

In a $8^{th}$ aspect according to at least one of the $6^{th}$ or the $7^{th}$ aspects, the first outlet is coupled to the post-infusion line and the second outlet is coupled to the pre-infusion line.

In a $9^{th}$ aspect according to at least one of the previous aspects from 5 to 8, wherein the first and second part of the infusion valve unit are made of a single piece or are firmly joined one to the other.

In a $10^{th}$ aspect according to at least one of the previous aspects, the second part further comprises a valve seat and a sealing element mounted to the valve seat.

In a $11^{th}$ aspect according to the previous aspect, the valve seat has a central opening and at least one fluid channel.

In a $12^{th}$ aspect according to the $10^{th}$ or $11^{th}$ aspect, the sealing element has a stem extending through the central opening and a flexible structure extending radially from the stem and being configured to cover in a closed state the fluid channel.

In a $13^{th}$ aspect according to at least one of the previous aspects, the second part has a male connecting part and the first part has a female connecting part.

In a $14^{th}$ aspect according to the previous aspect, the second part has a circumferential seal at a part that is received by the female connecting part of the first part.

In a $15^{th}$ aspect according to the $13^{st}$ aspect, the first part includes a seal having an annular groove sized to receive a cylinder-shaped part of the valve unit.

In a $16^{th}$ aspect according to the $11^{th}$ aspect, the valve seat has a plurality of fluid channels arranged around the central opening.

In a $17^{th}$ aspect according to $11^{th}$ or $16^{th}$ aspect, the second part comprises a membrane chamber and a membrane arranged in the membrane chamber and the membrane chamber has an inner shape that allows the membrane to move between a first position, in which fluid flow through the fluid channel/s is enabled, and a second position, in which fluid flow through the fluid channel/s is blocked.

In a $18^{th}$ aspect according to the previous aspect, the membrane chamber has an inner shape that is conical with a larger diameter at a side that faces an output chamber and a smaller diameter at a side that faces an input chamber.

In a $19^{th}$ aspect according to at least one of the previous aspects, the first part includes a bypass port coupled to a bypass line, and wherein the first part is configured to be covered by a cap, wherein the cap closes a bypass for fluid used during disinfecting and rinsing the system.

In a $20^{th}$ aspect according to at least one of the previous aspects, the valve unit delimits an input chamber provided with the inlet and an output chamber provided with the first and second outlets, wherein the input chamber and the output chamber are separated by a sealing mechanism.

In a $21^{st}$ aspect according to the previous aspects, the input chamber is cylindrical.

In a $22^{nd}$ aspect according to at least one of the previous aspects 20 or 21, the output chamber is cylindrical.

In a $23^{rd}$ aspect according to at least one of the previous aspects 21 or 22, the output chamber and the input chamber are reciprocally coaxial.

In a $24^{nd}$ aspect according to at least one of the previous aspects from 21 to 23, the first and the second outlets are orthogonal with respect to a main axis of the output chamber.

In a $25^{th}$ aspect according to at least one of the previous aspects from 21 to 24, the first and the second outlets develops orthogonally with respect to an outer surface of the output chamber.

In a $26^{th}$ aspect according to at least one of the previous aspects from 21 to 25, the inlet is aligned with respect to a main axis of the input chamber.

In a $27^{th}$ aspect according to at least one of the previous aspects from 20 to 26, the output chamber is larger than the input chamber.

In a $28^{th}$ aspect according to at least one of the previous aspects from 20 to 27, the first and the second outlets are substantially tangential with respect to a cylindrical inner surface of the output chamber.

In a $29^{th}$ aspect according to at least one of the previous aspects, a bypass port develops from a first part of the valve unit and parallel to the first and the second outlets.

In a $30^{th}$ aspect according to at least one of the previous aspects, the first and the second outlets are parallel to each other.

In a $31^{st}$ aspect according to at least one of the previous aspects, the first and the second outlets are orthogonal with respect to the inlet.

In a $32^{nd}$ aspect according to at least one of the previous aspects, the infusion valve unit is made of rigid (i.e. plastic) material, the stiffness of the material of the valve unit being such to support the infusion lines without deforming said valve unit. The first and second outlets are each defined by tubular portions of said material developing from an outer surface of the valve unit. The inlet is defined by a tubular portion developing from the first part of said valve unit.

In a $33^{rd}$ aspect according to at least one of the previous aspects the valve unit presents an outer surface structured or textured to allow secure gripping.

In a $34^{th}$ aspect according to at least one of the previous aspects, the infusion pump is arranged inside a housing of the extracorporeal blood treatment system.

In a $35^{th}$ aspect according to at least one of the previous aspects, the infusion pump is a non-occlusive pump.

In a 36th aspect according to at least one of the previous aspects, clamps are arranged on the infusion circuit, wherein each clamp has an open state to allow fluid flow and a closed state to block fluid flow.

In a 37th aspect according to at least one of the previous aspects, the first part constitutes an infusion port.

A 38th aspect relates to an extracorporeal blood treatment system comprising a disposable set according to one or more of the previous aspects.

In a 39th aspect according to at least one of the previous aspects, the disposable set comprises an air trap inserted in the blood return line.

In a 40th aspect according to the previous aspect, the air trap comprises a box delimiting a chamber closed by a cap.

In a 41st aspect according to the previous aspect, the post infusion line is connected to the blood return line in the air trap.

In a 42nd aspect according to the 40th or 41st aspect, the post infusion line enters the air trap and opens into the box of the air trap through the cap of said air trap.

In a 43rd aspect according to at least one of the previous aspects from 39th to 42nd, the blood withdrawal line is joined and supported by the air trap.

In a 44th aspect according to at least one of the previous aspects from 40th to 43rd, the blood withdrawal line is supported by the cap of the air trap.

In a 45th aspect according to at least one of the previous aspects from 40th to 44th, the blood withdrawal line passes through the cap of the air trap and is not in fluid communication with the chamber of the air trap.

In a 46th aspect according to at least one of the previous aspects from 39th to 45th, the pre-infusion line is connected to the blood withdrawal line at the air trap.

In a 47th aspect according to at least one of the previous aspects from 40th to 46th, the pre-infusion line enters the blood withdrawal line passing into the cap of the air trap.

In a 48th aspect according to at least one of the previous aspects from 40th to 47th, the pre-infusion line and the blood withdrawal line connect to each other at a joint made into the cap of the air trap.

In a 49th aspect according to at least one of the previous aspects from 40th to 48th, the pre-infusion line presents a first end connected to the second outlet of the second part of the infusion valve unit and a second end joined to the cap of the air trap.

In a 50th aspect according to at least one of the previous aspects from 40th to 49th, the post-infusion line presents a first end connected to the first outlet of the second part of the infusion valve unit and a second end joined to the cap of the air trap.

In a 51st aspect, the disposable set comprising the blood withdrawal line, the blood return line, the air trap, the pre-infusion line, the post infusion line and the second part of the infusion valve unit is stored in a single packaging prior to use.

In a 52nd aspect, the blood withdrawal line, the blood return line, the air trap, the pre-infusion line, the post infusion line and the second part of the infusion valve unit are joined each other prior to use.

The improved technology provides for improved reliability and handling of the extracorporeal blood treatment system because only one infusion port for both pre- and post-infusion is present to which an operator needs to connect the infusion line set. When setting up the system for a treatment with pre- and/or post infusion, the operator removes in one embodiment a cap from the valve unit's first part and connects the second part to it. As only one component needs to be connected, the set-up time and the risk for misconnections are reduced.

The improved disposable of the invention provides for easy handling and improved safety and reliability too, because the operation of setting up the system for a treatment is greatly simplified. The operator needs only to unpackage the disposable and to connect the blood lines to the treatment unit and the second part of the infusion valve unit to the first part of said valve unit already mounted on the housing or to connect the valve unit to the connector on the housing.

As to the term "infusion port", it is contemplated that it is a matter of definition what is considered to be the infusion port. That is, the valve unit's first part alone may be considered to be the system's infusion port. Alternatively, the valve unit as a whole (i.e., with both parts) may be considered to be the system's infusion port.

Advantageously, the handling is further improved because the valve unit integrates several functions into one unit: it is or forms an infusion port, it allows fluid to pass only in one direction, and implements a T-connector. For example, the operator does not have to handle a further T-connector to couple infusion fluid into the extracorporeal blood circuit.

Additionally, as the one-way valve is positioned in the second part, which in use is connected to an infusion line, reduces or even eliminates the problem of dripping when undressing the system after its use. It is a further advantage that the valve unit is a passive component so that no additional control mechanism is required; opening and closing of the valve is caused by pressure drops.

Further, the integrated one-way valve ensures that any fluid that may have been in contact with the patient or the patient's blood cannot enter the first part of the valve unit, and, hence, non-disposable parts of the system. As is known in the art, disposables are, e.g., those components of the system that are in contact with the patient's blood (e.g., the extracorporeal blood circuit, or the treatment unit) during a treatment session, and that are usually replaced thereafter.

The improved technology provides flexibility regarding selecting a particular valve mechanism. One exemplary valve mechanism is based on a combination of a valve seat with at least one fluid channel, and a sealing member having a stem and a disc-shaped structure radially extending from one end of the stem. The disc-shaped structure is configured to extend beyond the fluid channel to cover it in a closed state.

Another exemplary valve mechanism is based on a combination of a valve seat with at least one fluid channel, and a membrane arranged in a membrane chamber. Within the membrane chamber, the membrane is movable to either prevent fluid to flow through the fluid channel, or to allow such fluid flow. Such a membrane has a low forward flow pressure, and closing of the valve occurs with a very low pressure difference.

In one embodiment, the infusion pump is located inside the system housing and connected to the valve unit's first part. As the infusion pump is located internally, space is freed up on the outside of the housing so that, e.g., cleaning is facilitated.

Further, locating the infusion pump inside the housing allows use of a non-occlusive pump, e.g., a gear pump that uses rotating gears to transport a fluid. Inserting a tube of the extracorporeal blood circuit through a peristaltic pump is no longer required, which again reduces the time for setting-up the system. In addition, a gear pump generates less noise than a peristaltic pump so that the patient is no longer exposed to the periodic sound caused by the rollers of a peristaltic pump.

It is a further advantage of the improved technology that the valve unit allows using a non-occlusive pump. A peristaltic pump inherently prevents backflow of fluid, but a gear pump does not have such an inherent characteristic. To protect the system from such backflow, the valve unit includes a one-way valve for which various configurations are possible.

In one embodiment, the valve unit has a bypass port at the first part, wherein the bypass port is coupled to a bypass line. When the second part is not connected, a cap is placed on top of the first part. With the cap placed, the first part is not only protected against damage and/or contamination, but also sealed. The cap therefore closes a bypass for fluid that may be used, e.g., during disinfection and/or rinsing of the system.

The novel features characteristic of the invention are set out in the claims below. The invention itself, however, as well as other features and advantages thereof, are best understood by reference to the detailed description, which follows, when read in conjunction with the accompanying drawings, wherein:

Figure 1:
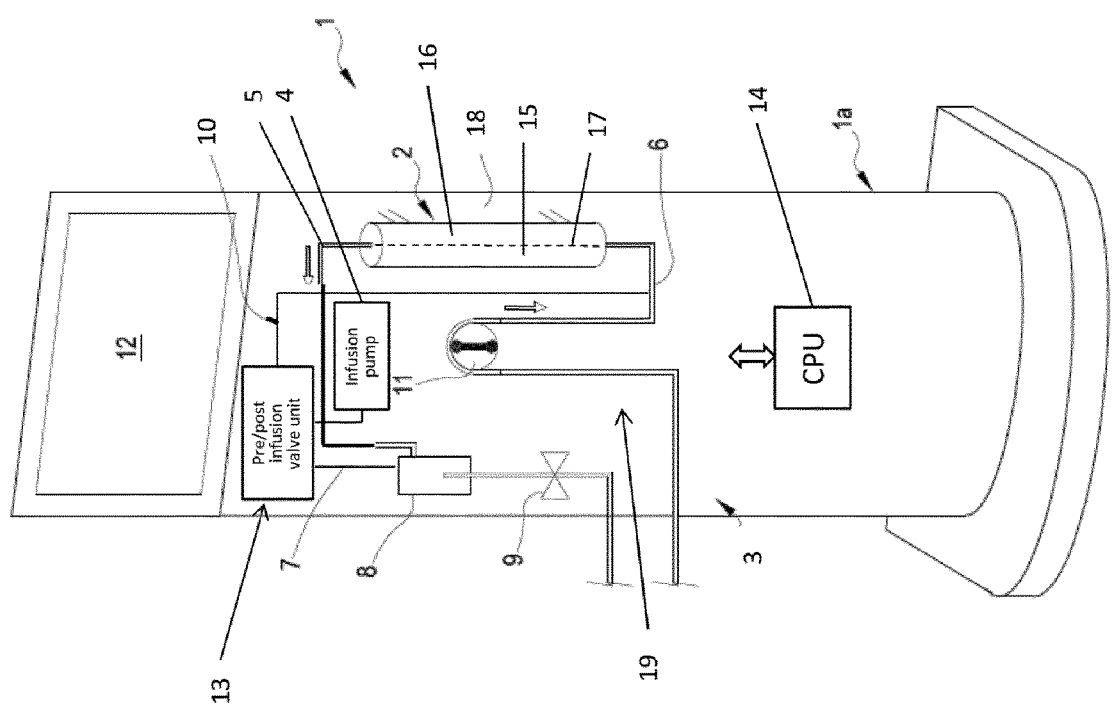
FIG. 1 shows a schematic illustration of one embodiment of an extracorporeal blood treatment system having a pre-/post-infusion valve unit.

FIG. 1 is a schematic illustration of one embodiment of an extracorporeal blood treatment system in which the improved technology described herein is implemented. The illustrated system has an extracorporeal blood treatment apparatus 1 (also referred to as "apparatus 1") having a housing 1a, a user interface 12, a (blood) pump 11 and a control unit 14 (labeled as CPU in FIG. 1). Further, the housing 1a holds a treatment unit 2, and components of an extracorporeal blood circuit 3 such as a blood return line 5, a blood withdrawal line 6 and an air trap 8 inserted in the blood return line 5 that feeds treated blood back to a patient. The user interface 12 may include a display screen and a keypad, a touch screen or a combination thereof. For ease of illustration, a fluid circuit for a dialysis fluid is not shown in FIG. 1, but the illustration of the system in FIG. 2 shows such a dialysis fluid circuit.

In the embodiment of FIG. 1, the system includes further a pre-/post-infusion valve unit 13 (hereinafter referred to as "valve unit 13") and an infusion pump 4, wherein the valve unit 13 is coupled to the infusion pump 4 and via pre-infusion line 10 and post-infusion line 7 to the extracorporeal blood circuit 3. The valve unit 13 is used when the patient's treatment requires pre-infusion or post-infusion or a combination of pre- and post-infusion. For the sake of completeness, additional details regarding various optional embodiments of the extracorporeal blood circuit 3 and associated components, such as sensors and actuators, are described below.

Figure 2:
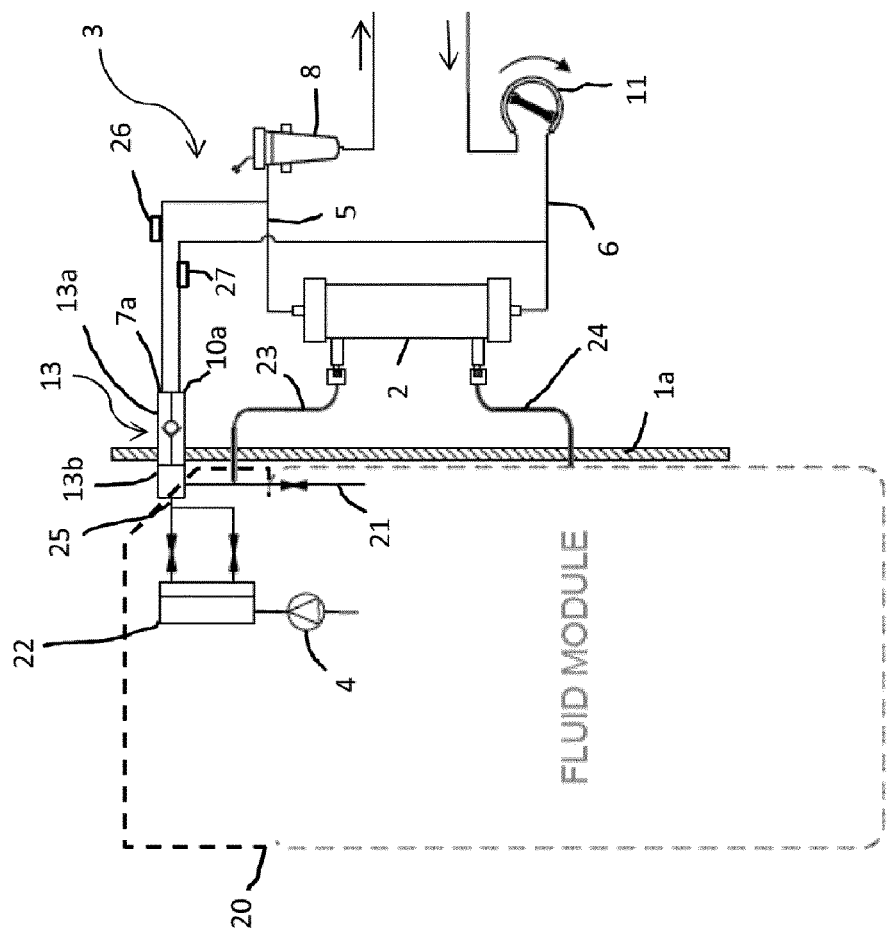
FIG. 2 is a simplified illustration of the system shown in FIG. 1 with the valve unit mounted to a housing of the system and coupled to an internal infusion pump.

FIG. 2 shows a simplified illustration of the system shown in FIG. 1, wherein the valve unit 13 is mounted to the housing 1a of the apparatus 1, and coupled to the infusion pump 4 and the extracorporeal blood circuit 3. The housing 1a is represented by a cross-section of a housing wall (hatched area) to indicate components located inside the housing 1a (left side) and components located outside the housing 1a (right side).

A fluid module 20 is located inside the apparatus 1 and includes the infusion pump 4, an ultra-filter 22 for removing particles and/or bacteria from the infusion liquid to obtain a pure infusion liquid, a fluid line 21 (also referred to as "bypass line") and access ports for lines 23, 24 of the dialysis fluid circuit. As shown, the infusion pump 4 is located inside the apparatus 1, and the ultra-filter 22 is connected between the valve unit 13 and the infusion pump 4. The fluid module 20 is generally configured to handle fluids other than blood and to perform a variety of functions, such as providing the infusion fluid to the external blood circuit 3 on the outside of the apparatus 1, and providing the dialysis fluid for supply to the treatment unit 2 on the outside. For these purposes, the fluid module 20 at least controls the flow of these fluids. Depending on a particular embodiment of the apparatus 1, the fluid module 20 may perform additional functions, such as preparing a fluid, e.g., the dialysis fluid, disposing of used dialysis fluid, priming the system and other functions known to the skilled person.

The term "fluid module" is used herein in a non-limiting way. That is, although the fluid module 20 is shown to be inside the apparatus 1, in certain embodiments some functions may have components located on the outside of the apparatus 1, e.g., the lines 23, 24 connected to the treatment unit 2, or the infusion lines 7, 10 connected to the extracorporeal blood circuit 3. Those skilled in the art will appreciate that it is a matter of definition and design choice whether or not certain components, regardless of where they are located in a particular embodiment, are viewed as a part of the fluid module 20. For that reason, the fluid module 20 is shown in FIG. 2 by means of dashed lines.

On the outside of the apparatus 1, the infusion line 7 connects the valve unit 13 to the blood return line 5 to allow post-infusion, and the infusion line 10 connects the valve unit 13 to the blood withdrawal line 6 to allow pre-infusion. Although the infusion line 7 is in FIG. 2 connected to the blood return line 5 upstream of the air trap 8, it is contemplated that in another embodiment the infusion line 7 may be connected to the air trap 8. In both embodiments, the air trap 8 ensures that treated blood is essentially free of air bubbles before it is returned to the patient.

A clamp 26, 27 is provided on each infusion line 7, 10 and configured to allow or interrupt fluid flow through the respective infusion line 7, 10. In one embodiment, the clamps 26, are manually operated. That is, depending on whether the patient's treatment includes pre- or post-infusion, or both, the operator opens or closes the clamps 26, 27. In another embodiment, the clamps 26, 27 are configured to be actuated by the control unit 14. It is contemplated that the skilled person is familiar with the various kinds of clamps.

Also on the outside of the apparatus 1, the treatment unit 2 is connected to the dialysis fluid circuit. The line 23 of the dialysis fluid circuit feeds the dialysis fluid to the treatment unit 2, and the line 24 guides used dialysis fluid away from the treatment unit 2. As is known in the art, in the treatment unit 2 the dialysis fluid and the blood flow in opposite directions.

As shown in FIG. 2, the valve unit 13 extends through the housing wall. As described in more detail with reference to the various embodiments shown in FIGS. 3-6, the valve unit 13 has a first part 13b and a second part 13a that is releasable connectable to the first part 13b. The first part 13b is mounted on the housing 1a, and has an inlet 25 coupled to the infusion pump 4. The first part 13b forms or is part of an infusion port. The second part 13a has a first outlet 7a coupled to the infusion line 7 and a second outlet 10a coupled to the infusion line 10. The infusion lines 7, 10 are part of an infusion circuit which is configured to couple to the extracorporeal blood circuit 3.

The second part 13 includes a one-way valve configured to allow infusion liquid to flow from the inlet 25 towards at least one of the first and second outlets 7a, 10a, and to block fluid (back) flow towards the inlet 25. A one-way valve is also known as check valve, clack valve or non-return valve, and allows fluid (liquid or gas) to flow through it in only one direction. Various embodiments of a one-way valve are shown in FIGS. 3-6 and described below.

Figure 3:
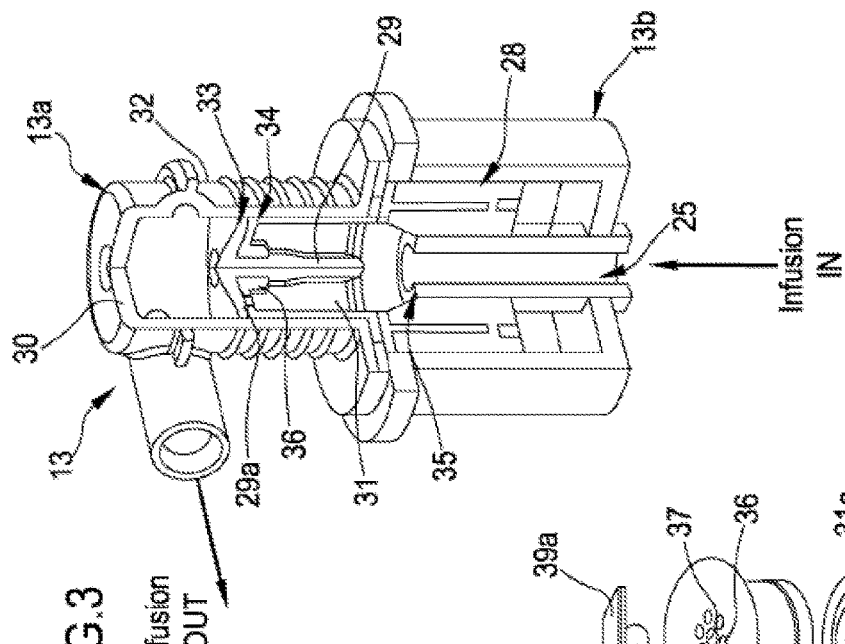
FIG. 3 is a schematic perspective view of one embodiment of a valve unit having a first valve structure.
Figure 4:
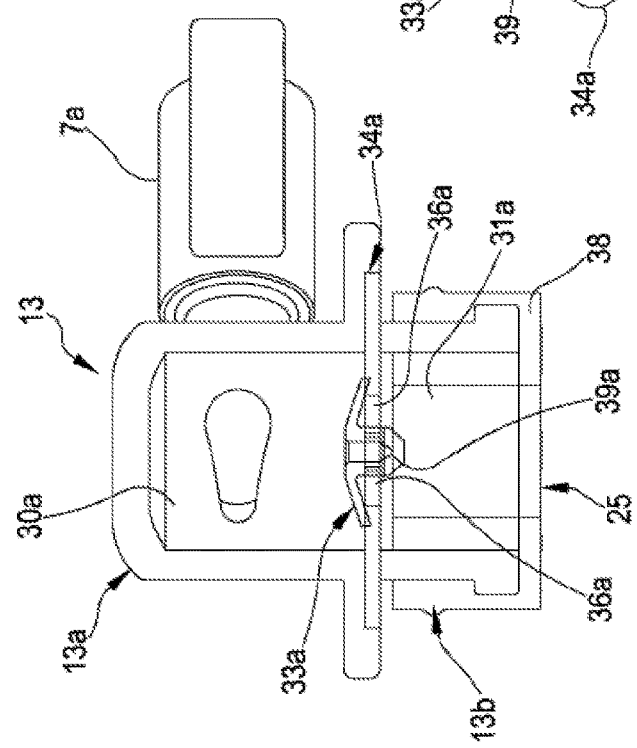
FIG. 4 is a schematic cross-sectional view of one embodiment of a valve unit having a second valve structure.

In the embodiments shown in FIGS. 3 and 4, the one-way valve is a normally-closed valve, i.e., the valve is closed unless the pressure at which the infusion fluid is pumped in direction of the valve unit 13 exceeds a predetermined pressure. This predetermined pressure is sometimes referred to as "cracking pressure" which is the minimum upstream pressure at which the valve will operate. Typically, a one-way valve is designed and specified for a specific cracking pressure.

As mentioned above, the first part 13b is installed on the apparatus 1, and the second part 13a can be connected to the first part 13b, e.g., by the operator when setting-up the system for an extracorporeal blood treatment. In use, the pressure caused be the infusion pump 4 when pumping the infusion liquid causes the one-way valve to open (i.e., the pressure exceeds the valve's cracking pressure) and the infusion fluid flows into at least one of the infusion lines 7, 10 depending on which clamp 26, 27 is open. As soon as the pressure drops below the cracking pressure, e.g., when the infusion pump 4 is stopped, the valve closes.

In its closed state, the valve prevents any fluid to flow or diffuse from an infusion line 7, 10 into the first part 13b of the valve unit 13. With that, the risk of backflow and/or cross-contamination is reduced. This is of particular importance in case a non-occlusive pump (e.g., a gear pump) is used as the infusion pump 4 instead of an occlusive pump (e.g., a peristaltic pump) as described below. An occlusive peristaltic pump inherently always pinches the tube and thereby prevents backflow. In contrast, a gear pump does not have such inherent function and under certain pressure conditions fluid could flow back towards the gear pump.

FIG. 2 further shows that the infusion lines 7, 10 connect via the second part 13a to the infusion port, but not directly. The first part 13b is thereby never in direct contact with the infusion lines 7, 10. The second part 13a, which is in contact with the infusion lines 7, 10, may be configured to be releasable from the infusion lines 7, 10 to facilitate cleaning and/or sterilizing. Alternatively, the second part 13a may be a disposable part that is replaced after use. In another embodiment, the second part 13a may be an integral part of the infusion lines 7, 10 forming a set for single or (after cleaning and/or sterilizing) multiple use. If the infusion port is not used, it is covered by a cap (not shown in FIG. 2) that protects the infusion port from contamination or damage. In addition, as described below with reference to FIGS. 5 and 7, the cap closes a bypass for fluid used to prime or disinfect the infusion port.

In the illustrated embodiment, the infusion pump 4 is located inside the apparatus 1 as shown in FIG. 2. It is contemplated, however, that the infusion pump 4 may be located at another location as well, e.g., on an outer area of the apparatus 1 or spaced from the apparatus 1. This applies to all embodiments of the valve unit 13 described herein.

The infusion pump 4 may have one of several configurations; for example, it may be a peristaltic pump or a gear pump. As is known in the art, in a peristaltic pump, fluid is contained within a flexible tube fitted inside a circular pump casing. A rotor with a number of "rollers" compresses the flexible tube, and, as the rotor turns, the part of the tube under compression is pinched closed (or "occludes"). The periodic pinching forces the fluid to be pumped to move through the tube. Additionally, as the tube opens to its natural state fluid flow is induced to the pump. In contrast, a gear pump has two external spur gears, or an external and an internal spur gear. As the gears rotate they separate on the intake side of the pump, creating a void and suction which is filled by fluid. The fluid is carried by the gears to the discharge side of the pump, where the meshing of the gears displaces the fluid.

Due to these different operating principles, the above-mentioned problems of backflow and cross-contamination are usually less critical in a system that uses a peristaltic pump to infuse a liquid than in a system that uses a gear pump. For example, the usually disposable tube prevents that the fluid gets into direct contact with the (non-disposable) pump or its parts. In a gear pump, in contrast, fluid is in direct contact with (non-disposable) parts of a gear pump. In spite of this, in certain applications a gear pump may be preferred over a peristaltic pump and allow new system configurations because gear pumps, for example, no longer need to be accessible to allow insertion of a fluid tube.

In the following description of certain embodiments of the extracorporeal blood treatment system, the infusion pump 4 is a gear pump. It is contemplated, however, that application of the improved technology described herein is not limited to a gear pump, and may be used in connection with a peristaltic pump as well.

FIG. 3 is a schematic perspective view of one embodiment of the valve unit 13 having a first valve structure, with a section removed to show internal components of the valve unit 13. Due to the removal of the section only one outlet (7a) is shown, however, it is contemplated that the valve unit 13 has two outlets 7a, 10a, as shown in FIG. 2. Further, for ease of illustration, the valve unit 13 is shown without being attached to the apparatus 1 or being connected to the infusion lines 7, 10, however, it is contemplated that the first part 13b of the valve unit 13 is mounted to the apparatus 1.

In the embodiment of FIG. 3, the second part 13a is configured to have a male connecting part, and the first part 13b is configured to have a female connecting part. The female connecting part receives the male connecting part in a releasable and sealing manner. For that purpose, at least one of the male and female connecting parts has a seal. In the illustrated example, the second part 13a has a circumferential seal 28 at the part that interacts with the first part 13b. The seal 28 may be made of silicon or other suitable material. It is contemplated that other locking and sealing mechanisms such as a Luer lock, a screw connection, a bayonet coupling or other suitable locking mechanisms known to the skilled person may be used.

Further, the second part 13a is contoured to have an outer surface 32 that may be sized to allow manipulation by the operator, and that may be structured or textured to allow secure gripping by the operator. In FIG. 2, the outer surface 32 has circumferential ribs; however, any other suitable structures may be used. Regarding the contour of the valve unit 13 shown in FIG. 3, it is contemplated that the structure and dimension of the outer surface 32 can be selected to a meet certain space and/or handling requirements. This applies also to the embodiments shown in FIGS. 4-6. The particular contours shown in these figures are, therefore, exemplary and not to be viewed as limiting.

The second part 13a has a generally cylindrical hollow body, in which a valve seat 34 and a sealing member 33 are positioned. The valve seat 34 and the sealing member 33 (sealing mechanism) divide the internal space into an output chamber 30 and an input chamber 31. The output chamber 30 is in fluid communication with the outlets 7a, 10a, and the input chamber 31 is in fluid communication with the inlet 25 of the valve unit 13. The input chamber 31 and the output chamber 30 are cylindrical and coaxial (provided with the same main axis of the cylinder).

The valve seat 34 has a platform that is attached to the body of the second part 13a. In one embodiment, the valve seat 34 is a hollow cylinder that is open on a side that faces the first part 13b and that has the platform on the opposite side. Further, the valve seat's platform has a central opening through which a stem 29 of the sealing member 33 extends from the output chamber 30 into the input chamber 31. The stem 29 thereby secures the sealing member 33 to the valve seat 34. At an end of the stem 29 that faces the output chamber 30, the stem 29 has a radially extending, generally disc-shaped structure 29a. The disc-shaped structure is made of a flexible material that is biocompatible, e.g., silicon. The disc-shaped structure 29a may be referred to as a diaphragm.

As shown in FIG. 3, the sealing member 33 with such a stem 29 and disc-shaped structure 29a has a generally T-shaped cross-section. Again, as shown in FIG. 3, the disc-shaped structure 29a has a cross-section with a curved (e.g., convex) upper surface that faces the output chamber 30 and a flat or slightly curved (e.g., concave) lower surface that faces the valve seat 34. When viewed from a side, the sealing member 33 has a general shape that resembles an umbrella.

The valve seat 34 (on the platform side) has at least one fluid channel to allow passage of the infusion liquid. The function of allowing passage of the infusion liquid may be achieved in a variety of ways. In one exemplary embodiment, several fluid channels are arranged in a circle around the central opening. The disc-shaped structure 29a of the sealing member 33 is configured and sized to extend over the fluid channels. In a closed position of the valve unit 13, the structure 29a covers the fluid channels and prevents passage of the infusion fluid. The central opening and the fluid channels may be arranged as in the embodiment described with reference to FIGS. 4 and 4a. However, it is contemplated that more or less fluid channels in various arrangements may be used in a particular embodiment.

In such a check valve, the sealing member 33 is positioned to create a normally-closed valve. Pressure on the upstream side must be greater than the pressure on the downstream side by a certain amount, known as the pressure differential, for the check valve to open allowing flow. Once positive pressure stops, such a diaphragm-like structure automatically flexes back to its original closed position.

More particularly, the valve unit 13 of FIG. 3 is in the closed position when the pressure in the input chamber 31 is below the cracking pressure. If the pressure in the input chamber 31 exceeds the cracking pressure, the infusion fluid pressure urges the structure 29a towards the output chamber 30 uncovering the one or more fluid channels and opening the valve unit 13.

Referring to the (female) first part 13b, this part is configured to allow its mounting to the housing 1a, to secure the second part 13a, which extends at least partially into the first part 13b, and to allow passage of the infusion fluid from the inlet 25 to the input chamber 31. For the mounting function, the first part 13b has in one embodiment a cylindrical body that fits into a correspondingly sized opening in the wall of the housing 1a. When inserted into the opening, a rim with a larger diameter presses from the outside against the wall to secure the body in the housing 1a in combination with a counter screw or other retaining mechanism. For the fluid-passage function, the first part 13b has a channel 35 that extends between the inlet 25 and the input chamber 31. In addition to the securing function, the first part 13b is configured to provide in combination with the second part 13a for a fluid tight seal, as described above.

As can be seen in FIG. 3, the channel 35 is coaxial with respect to the inlet 25 and to the input and output chambers 31, 30 while the first and the second outlets 7a, 10a are parallel to each other and orthogonal with respect to the common main axis of the input chamber 31, of the output chamber 30, of the channel 35 and of the inlet 25.

Figure 4A:
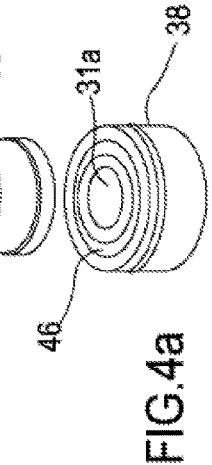
FIG. 4a is a schematic perspective view of components of the second valve structure.

FIG. 4 is a schematic cross-sectional view of another embodiment of a valve unit 13 having a second valve structure, and FIG. 4a shows components of the second valve structure. As in FIG. 3, only one outlet (7a) is shown, although the valve unit 13 has two outlets 7a, 10a, as shown in FIG. 2. Also, the valve unit 13 is again shown without being attached to the apparatus 1 or connected to the infusion lines 7, 10, however, it is contemplated that the first part 13b of the valve unit 13 is mounted to the apparatus 1. Further, the (female) first part 13b and the (male) second part 13a interact in a releasable and sealing manner, and may have complementary locking mechanism as described above with reference to FIG. 3.

Referring to FIG. 4 and FIG. 4a, the valve unit 13 has a valve seat 34a that is attached to the second part 13a. The valve seat 34a has a platform that is attached to the body of the second part 13a. In one embodiment, the valve seat 34a includes further a hollow cylinder that extends from the platform towards the first part 13b and is open on that side (i.e., opposite the platform). On the open side, the cylinder has a flange.

The valve seat 34a has a sealing member 33a that is mounted by means of a stem 39 to a central opening 37 of the valve seat 34a. The valve seat 34a has fluid channels 36a, which extend between the output chamber 30a and the input chamber 31a, and are, for example, arranged in a circle around the central opening 37. In the illustrated embodiment, the central opening 37 and the fluid channels 36a are implemented in the valve seat's platform.

The sealing member 33a has a generally T-shaped cross-section and a flexible disc-shaped structure 39a that is sized to cover the fluid channels 36a in a normally-closed state. The structure 39a has a cross-section with a curved (e.g., convex) upper surface that faces the output chamber 30a and a flat or curved (e.g., concave) lower surface that faces the valve seat 34a. When viewed from a side, the sealing member 33a has a general shape that resembles an umbrella.

The stem 39 of the sealing member 33a shown in FIG. 4 is shorter than the stem 29 of the sealing member 33 shown in FIG. 3. The valve unit 13 can therefore be built smaller. Further, the volume of the input chamber 31a is lower than the volume of the input chamber 31 of FIG. 3.

In the embodiment of FIG. 4 and FIG. 4a, the first part 13b includes a seal 38 made of an elastic material, e.g., silicon. The seal 38 has an annular groove 46 sized to receive the valve seat's cylinder part with its flange. The elasticity of the material provides for proper sealing and for a snug fit between the seal 38 and the valve seat 34a, as is visible in FIG. 4. The seal 38 has further a through hole that is aligned with the central opening 37 and the fluid passages 36a of the valve seat 34a. In use, infusion fluid flows from the inlet 25 through the through hole and the fluid channels 36a.

In one embodiment, the seal 38 constitutes the first part 13b. That is, it is the part that is mounted to the housing 1a, e.g., by inserting the seal 38 directly inserted into an opening in the housing 1a. In another embodiment, the seal 38 may be inserted into a casing so that the seal 38 and the casing constitute the first part 13b. The through hole of the seal 38 corresponds to the input chamber 31a.

In the embodiment of FIGS. 4 and 4a, the output chamber 30a is larger than the input chamber 31a.

Figure 6:
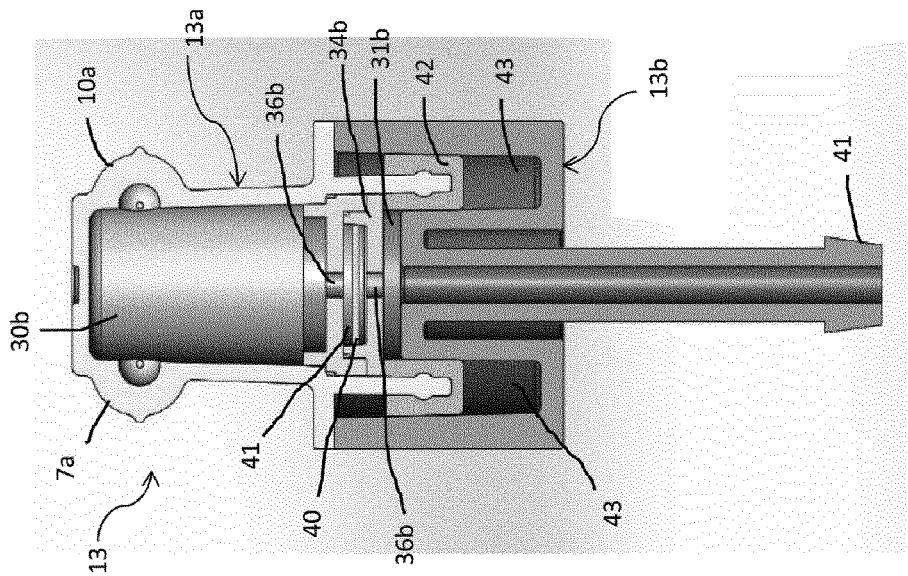
FIG. 6 is a schematic cross-sectional view of one embodiment of a valve unit having the third valve structure.
Figure 5:
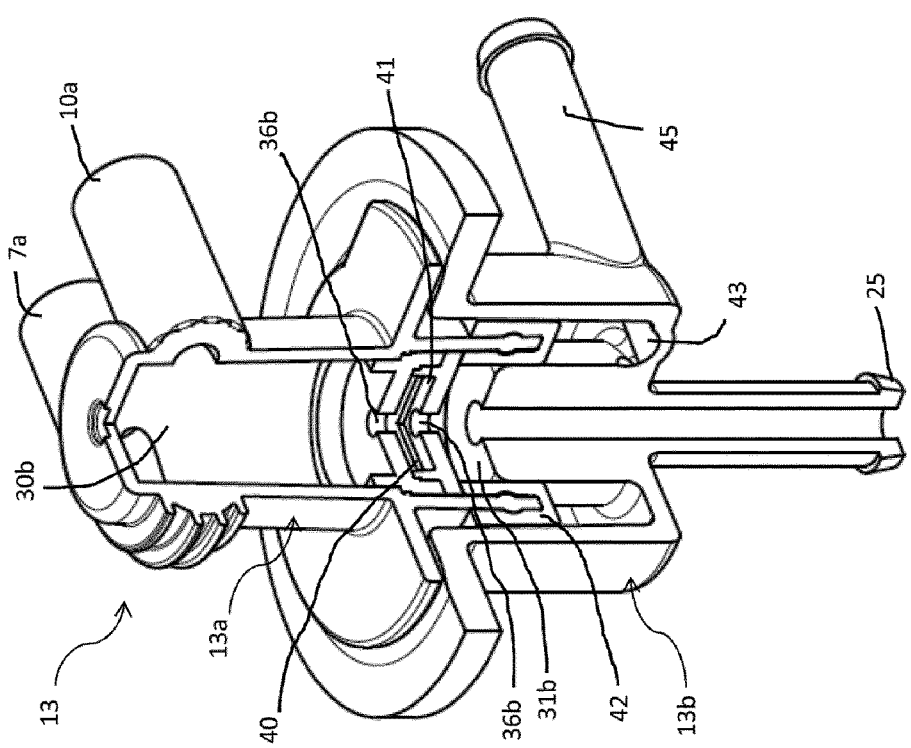
FIG. 5 is a schematic perspective view of one embodiment of a valve unit having a third valve structure and a bypass line.
Figure 7:
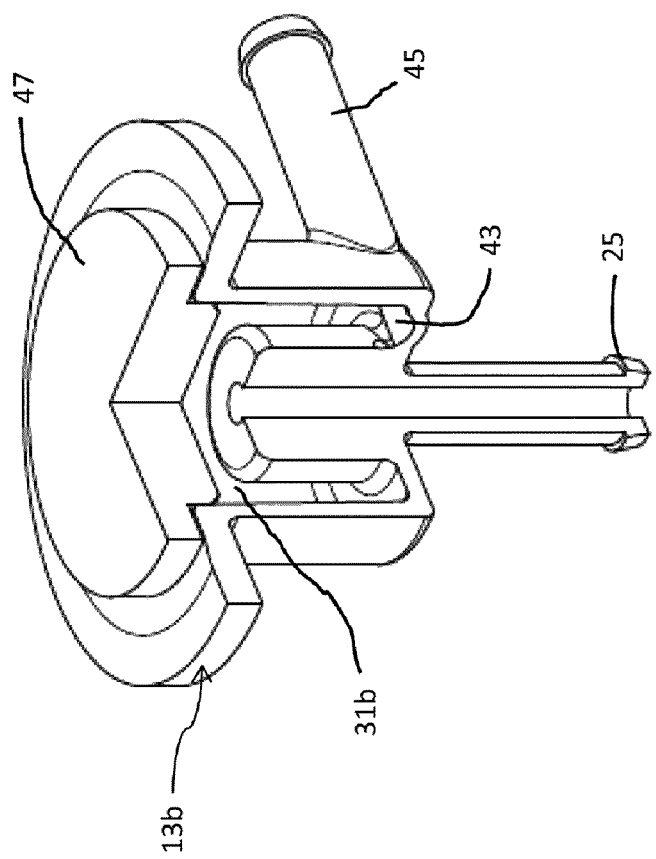
FIG. 7 is a schematic cross-sectional view of one embodiment of a valve unit having the third valve structure with a cap.

FIG. 5 is a schematic perspective view of one embodiment of a valve unit 13 having a third valve structure and a bypass port 45; and FIG. 6 is a schematic cross-sectional view of the valve unit 13 of FIG. 5. The bypass port 45 is optional, and FIG. 6 does not show a bypass port. It is contemplated that the embodiments shown in FIGS. 3 and 4 may have a bypass port as well. FIG. 7 shows the embodiment of FIG. 5 with the second part 13a removed and the first part 13b being covered by a cap 47. The cap 47 not only protects the infusion port from damage and/or contamination, it also closes a bypass for fluid used during disinfecting and rinsing the apparatus 1.

The third valve structure is based on a sealing mechanism that is different from those sealing mechanisms described with reference to FIGS. 3 and 4. That is, the sealing mechanism is based on a membrane principle. A membrane 40, e.g., disc-shaped, is positioned in a circular membrane chamber 41 of a valve seat 34b. The valve seat 34b is attached to the second part 13a which is inserted into the (female) first part 13b. As shown in FIG. 5, a ring seal 42 is attached to an end section of the second part 13 that is inserted into the first part 13b. When the first and second parts 13b, 13a are connected, a cavity 43 remains between the ring seal 42 and a bottom of the first part 13b. As shown in FIG. 5, the bypass port 45 is mounted to be in fluid communication with the cavity 43. When the infusion port is not in use and, hence, is covered by a cap, fluid can flow from the inlet 25 towards the cap and the cavity 43, and then into the bypass port 45.

The valve seat 34b has a fluid channel 36b that extends between a side facing the output chamber 30b and a side facing the input chamber 31b. Within the valve seat 34b, the membrane chamber 41 is inserted into the fluid channel 36b. Depending on the position of the membrane 40, fluid flow through the fluid channel 36b and the membrane chamber 41 is either enabled or blocked.

The membrane chamber 41 has an inner shape that allows the membrane 40 to move back and forth (in FIG. 5, up and down) within the membrane chamber 41. In one embodiment, the inner shape is conical with a larger diameter at the side that faces the output chamber 30b (this side is in FIG. 5 an upper side) and a smaller diameter at the side that faces the input chamber 31b (this side is in FIG. 5 a lower side). Depending on the fluid pressure or flow, the membrane 40 moves either towards the (larger diameter) upper side that faces the output chamber 30b, i.e., the valve opens, or towards the (smaller diameter) lower side that faces the input chamber 31b, i.e., the valve closes. To avoid that the membrane 40 closes the fluid channel 36b when it moves towards the upper side, ribs, protrusions or other suitable structures on the upper side prevent that the membrane 40 covers the fluid channel 36b and interrupts flow of the infusion fluid.

In the embodiment of FIGS. 5 and 6, the output chamber 30a is much larger than the input chamber 31a. Furthermore, as shown in FIG. 6, the main axes of each of the first and the second outlets 7a, 10a are substantially tangential with respect to a cylindrical inner surface of the output chamber 30b.

For the sake of completeness, the following describes other structural and operational aspects of the extracorporeal blood treatment system. The control unit 14 is configured or programmed to operate the apparatus 1 during all stages of a treatment. For that purpose, the control unit 14 has a (central) processing unit (CPU) coupled to or containing a data storage for storing computer-readable instructions/programs or data. The data storage may comprise a mass storage device based on one of a variety of technologies, for example, optical or magnetic, a re-programmable memory (EPROM, FLASH) or other known storage media. In addition, the control unit 14 is coupled to the user interface 12 and other components of the apparatus 1 by means of a communications bus or control lines, or a combination thereof.

For example, during the set-up stage, the control unit 14 communicates with the user interface 12 to enable entry of patient-specific data (personal and prescription data (e.g., kind of therapy (HD, HDF, HF), dialysis target values, dialysis duration). In one embodiment, the control unit 14 activates a communications device to read data from a patient card. During the treatment stage, i.e., when the patient is connected to the apparatus 1 and blood flows through the extracorporeal blood circuit 3, the control unit 14 controls operation of the pump 11, sensors and actuators according to the prescribed therapy (e.g., HD, HDF, HF, with or without pre-/post infusion), processes control parameters (e.g., sensor readings, actuator settings), and displays one or more of the processing results, sensor readings and actuator settings on a screen of the user interface 12.

Returning to the structure of the system 1 shown in FIG. 1, the treatment unit 2 has a primary chamber 15 and a secondary chamber 16 separated by a semipermeable membrane 17. Depending on the therapy, the membrane 17 may be selected to have different properties and performances. For example, the treatment unit 2 may be configured as a hemofilter, a hemodiafilter, a plasma filter, or a dialysis filter. A blood withdrawal line 6 of the extracorporeal blood circuit 3 is connected to an inlet of the primary chamber 15, and a blood return line 5 of the extracorporeal blood circuit 3 is connected to an outlet of the primary chamber 15. The treatment unit 2 is replaceable mounted by a holder 18 to a front panel or a side panel of the housing 1a of the apparatus 1. Similarly, the extracorporeal blood circuit 3 is replaceable mounted by a holder 19 to a front panel or a side panel of the housing 1a.

In use, the blood withdrawal line 6 and the blood return line 5 are connected to a needle or to a catheter or other access device (not shown) which is then placed in fluid communication with the patient's vascular system, such that blood can be withdrawn through the blood withdrawal line 6, passed through the primary chamber 15 and then returned to the patient's vascular system through the blood return line 5.

An air separator, such as the bubble trap 8, is inserted into the blood return line 5. Moreover, a safety clamp 9 controlled by the control unit 14 may be present on the blood return line 5 downstream the bubble trap 8. A bubble sensor, for instance associated with the bubble trap 8 or coupled to a portion of the line 5 between the bubble trap 8 and the clamp 9 may be present. If present, the bubble sensor is coupled to the control unit 14 to enable the control unit 14 to cause closure of the clamp 9 in case a critical number of bubbles is detected, e.g., one or more bubbles above a safety threshold.

The withdrawal line 6 and return line 5 may include any one of the arterial and venous lines of known type used in an apparatus for hemodialysis or hemo(dia)filtration. In particular, the withdrawal line 6 and return line 5 may be equipped with and/or connected to various sensors and actuators of known type (for example, pressure sensors, blood presence sensors or patient presence sensors, liquid level sensors, air presence sensors, blood transport pumps, infusion liquid transport pumps, automatic block valves, liquid level regulation devices, etc.) for the control and monitoring of the circuit itself, and to various devices of known type (gas-liquid separation devices, removal-injection access sites, manual clamps, service lines, etc.) for performing various operations on the circuit.

Further, in one embodiment, a sensor may be arranged in the extracorporeal blood circuit 3 (e.g., located in the blood withdrawal line 6) to emit a signal that is indicative of a change of blood volume of the patient. Such a sensor may include, for example, an optical or acoustic sensor. In one embodiment, the blood volume sensor indicates blood volume changes. In use, the user may enter a predetermined value for the blood flow rate using the user interface 12, and the control unit 14 controls during the treatment the pump 11 based on the predetermined blood flow rate.

The extracorporeal treatment apparatus may further have a system for supplying a fresh treatment fluid in a predetermined composition. The supply system may comprise any of the supply systems of known type used to supply a dialysis and/or replacement fluid in a hemodialysis or hemo(dia)filtration apparatus (for example of the type with in-line preparation of the treatment fluid from water and concentrates of the type sourcing from a batch-type source such as one or more bags of fluid). The supply system may have a supply line connected to an inlet of a fluid chamber, a source of treatment fluid (batch-type or in-line preparation type) and a supply pump. The sensor is in this case connected to the supply line to take into account, when determining the individual's weight loss, the flow of the treatment fluid, in particular dialysis fluid entering the fluid chamber and/or possibly replacement fluid infused into the extracorporeal circuit 3. The source has a device for in-line preparation of a treatment fluid having a predetermined concentration. The preparation device may comprise any of the devices of known type used in a hemodialysis or hemo(dia)filtration machine. In particular the preparation device may prepare the treatment fluid starting from water and concentrates by using of one or more sensors, for example, an electrical conductivity sensor (or another type of sensor for determining the composition of the dialysis solution) in order to determine, in a known way, the composition of the prepared fluid. The structure and functioning of the preparation device is known.

Figure 8:
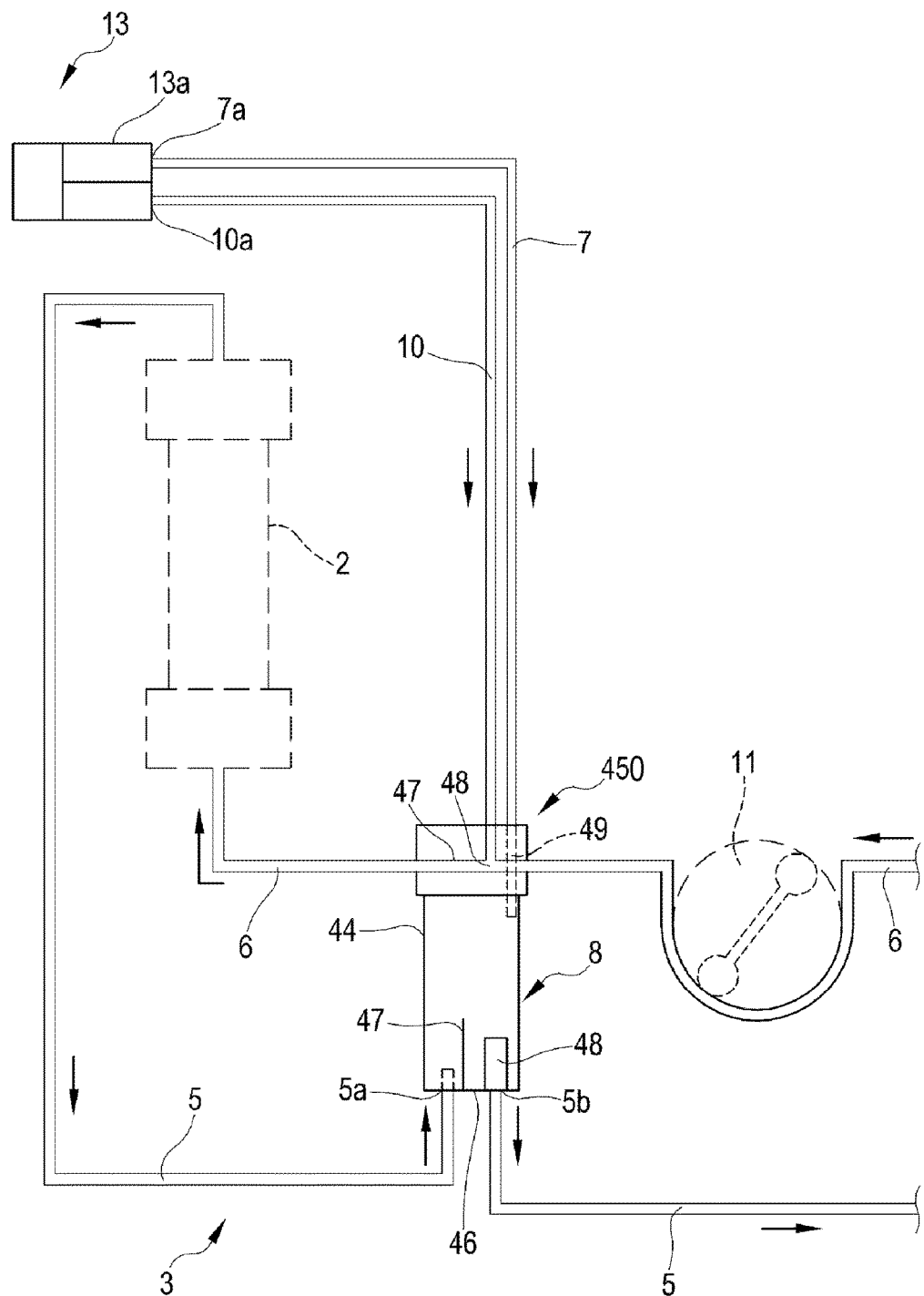
FIG. 8 is an embodiment of a disposable set of the system of FIGS. 1 and 2.

In one embodiment shown in FIG. 8, the extracorporeal blood circuit 3 with the withdrawal and return lines 6, 5 and the air trap 8, the infusion circuit comprising the pre and post infusion lines 10, 7 and the second part of 13a the infusion valve unit 13 form part of a disposable set which is replaced after use.

As shown in FIG. 8, the air trap 8 comprises a box 44 delimiting a chamber and closed by a cap 450. A bottom wall 46 of the box 44 is provided with an inlet 5a for a part of the return line 5 coming from the treatment unit 2. The bottom wall 46 is also provided with an outlet 5b for a part of the return line 5 going back to the vascular system of the patient P. The cap 450 closes an upper opening of the box 44. A partition wall 47 protrudes partially inside the chamber towards the cap 450 and separates the inlet 5a from the outlet 5b. A filter 48 is placed at the outlet 5b.

The cap 450 supports a section 47 of the blood withdrawal line 6. In particular, the blood withdrawal line 5 coming from the arterial vascular access enters the cap 450, passes through the cap 450 (by means of the section 47) and exits the cap 45 to reach the treatment unit 2. The section 47 and the blood withdrawal line 6 are not in fluid communication with the chamber of the box 44.

The pre-infusion line 10 presents a first end connected to the second outlet 10a of the second part 13a of the valve unit 13 and a second opposite end connected to the section 47 of the blood withdrawal line 6 at a T joint 48 made into the cap 450. The second end of the pre-infusion line 10 is joined to the cap 450.

The post-infusion line 7 presents a first end connected to the first outlet 7a of the second part 13a of the valve unit 13 and a second opposite end connected to the air trap 8. The cap 450 supports a section 49 of the post-infusion line 7 close to the second opposite end. The second end of the post-infusion line 7 opens into the box 44 passing through the cap 450, by means of said section 49 of the post-infusion line 7.

In other words, the cap 450 is shaped such as to define the section 47 of the blood withdrawal line 6, the T joint 48 and the section 49 of the post infusion line 7. The cap 450 is made of rigid plastic material. The stiffness of the material of the cap 450 is such to support the lines without deforming said cap 450.

The disposable set is pre-assembled in the sense that all its elements (blood withdrawal line 6, cap 450, blood return line 5, pre-infusion line 10, post-infusion line 7, second part 13a of the valve unit 13) are joined each other during manufacturing and stored and sold as an assembly in a single packaging.

In order to operate the system, the disposable set is mounted to the housing 1a of the apparatus 1. The treatment unit 2 is mounted to the housing 1a too. The extracorporeal blood circuit 3 is coupled to the treatment unit 2 and to the blood pump 11. The second part 13a of the infusion valve unit 13 is coupled to the first part 13b of the infusion valve unit 13.

In a further embodiment of the disposable set, not shown, said disposable set comprises the extracorporeal blood circuit 3 with the withdrawal and return lines 6, 5 and the air trap 8, the infusion circuit comprising the pre and post infusion lines 10, 7 and all the infusion valve unit 13. In this case, the first part 13b and the second part 13a of the infusion valve unit 13 can be a single body or can be firmly connected (not releasably connected). All the infusion valve unit 13 is part of the disposable set. The outlet 25 of said valve unit 13 comprises or is connected (by example through a section of pipe) to a connector which is releasably connectable to a connector mounted on the housing 1a of the blood treatment system. The connector on the housing can be firmly mounted on said housing or can be joined to a section of pipe coming from said housing.

In use, the hemodiafiltration apparatus operates in one embodiment in a known way to affect a predetermined weight loss in the patient, giving rise to an ultrafiltration device for ultrafiltering liquid from the blood chamber 15 to the fluid chamber 16 through the semipermeable membrane 17. In particular, the ultrafiltration is carried out by exploiting the pressure difference at the two sides of the membrane 17 (transmembrane pressure, or TMP) and the resulting convective transport of liquid generated by a discharge pump which enables having a pressure in the chamber fluid that is lower than the pressure in the blood chamber. The ultrafiltration means are of known.

The user interface 12 allows input of data, such as patient information, desired weight loss or desired weight loss rate, treatment time, significant parameters of the treatment and/or of the individual, etc. The user interface also displays and/or visually outputs data, such as patient information, treatment information and/or significant parameters of the treatment and/or of the individual, acoustic and/or visual alarms, etc.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the appended claims.

The invention claimed is:

1. Disposable set for an extracorporeal blood treatment system, comprising:
   an extracorporeal blood circuit comprising a blood withdrawal line and a blood return line configured to be coupled to a blood treatment device;
   an infusion circuit comprising infusion lines coupled to the extracorporeal blood circuit;
   an infusion valve unit configured to be releasably connectable to an infusion pump of the extracorporeal blood treatment system wherein the infusion lines of the extracorporeal blood treatment system comprise a pre-infusion line and a post-infusion line, the pre-infusion line connecting the infusion valve unit to the blood withdrawal line of the extracorporeal blood circuit and the post-infusion line connecting the infusion valve unit to the blood return line of the extracorporeal blood circuit, wherein the infusion valve unit comprises:
   a first outlet coupled to the post-infusion line and a second outlet coupled to the pre-infusion line;
   a one-way valve configured to allow infusion liquid to flow from an inlet towards at least one of the first and second outlets and to block fluid flow towards the inlet;
   an infusion valve unit body delimiting an input chamber in fluid communication with the inlet and an output chamber in fluid communication with the first outlet and the second outlet, wherein the input chamber and the output chamber are separated from each other within the infusion valve unit body by a seal, the infusion valve unit body being made of rigid material, the stiffness of the rigid material of the valve unit being such to support the post-infusion line and the pre-infusion line without deforming the infusion valve unit body, the first outlet and the second outlet being each defined by tubular portions of the rigid material projecting outward from an outer surface of the infusion valve unit body.

2. The disposable set of claim 1, wherein the infusion valve unit body comprises a first part and a second part, wherein the second part comprises the first outlet and the second outlet and is configured to be releasably connectable to a first part of the infusion valve unit body, wherein said first part comprises the inlet and is mounted on a housing of the extracorporeal blood treatment system such that the inlet and the first chamber are configured to receive infusion liquid from the infusion pump.

3. The disposable set of claim 1, comprising an air trap inserted in the blood return line.

4. The disposable set of claim 3, wherein the post-infusion line is connected to the blood return line in the air trap.

5. The disposable set of claim 3, wherein the blood withdrawal line is joined and supported by the air trap.

6. The disposable set of claim 3, wherein the pre-infusion line is connected to the blood withdrawal line at the air trap.

7. The disposable set of claim 3, wherein the post infusion line enters the air trap and opens into a box of the air trap through a cap of said air trap.

8. The disposable set of claim 3, wherein the pre-infusion line and the blood withdrawal line connect to each other at a joint made into a cap of the air trap.

9. The disposable set of claim 3, wherein the pre-infusion line presents a first end connected to the second outlet of the infusion valve unit and a second end joined to a cap of the air trap.

10. The disposable set of claim 3, wherein the post-infusion line presents a first end connected to the first outlet of the infusion valve unit and a second end joined to a cap of the air trap.

11. The disposable set of claim 1, wherein the first and the second outlets are parallel to each other and orthogonal with respect to the inlet.

12. The disposable set of claim 1, wherein the one-way valve comprises a valve seat and a sealing element mounted to the valve seat, wherein the valve seat has a central opening and at least one fluid channel, wherein the sealing element has a stem extending through the central opening and a flexible structure extending radially from the stem and being configured to cover the fluid channel when the sealing element is in a closed state.

13. The disposable set of claim 12, wherein the valve seat has a plurality of fluid channels arranged around the central opening.

14. The disposable set of claim 1, wherein the infusion valve unit body comprises a first part and a second part, wherein the second part a male connecting part, and the first part has a female connecting part configured to receive the male connecting part, and wherein the second part has a circumferential seal at a part that is received by the female connecting part of the first part.

15. The disposable set of claim 1, wherein the infusion valve unit body comprises a first part and a second part, wherein the second part has a male connecting part, and the first part has a female connecting part configured to receive the male connecting part, and wherein the first part includes a seal having an annular groove sized to receive a cylinder-shaped part of the male connecting part of the second part.

16. The disposable set of claim 1, wherein the infusion valve unit comprises a valve seat, a fluid channel, a membrane chamber and a membrane arranged in the membrane chamber, and wherein the membrane chamber has an inner shape that allows the membrane to move between a first position, in which fluid flow through the fluid channel is enabled, and a second position, in which fluid flow through the fluid channel is blocked.

17. The disposable set of claim 16, wherein the membrane chamber has an inner shape that is conical with a larger diameter at a side that faces an output chamber and a smaller diameter at a side that faces an input chamber.

18. The disposable set of claim 1, wherein the infusion valve unit includes a bypass port coupled to a bypass line, and wherein the first part infusion valve unit is configured to be covered by a cap, wherein the cap closes a bypass for fluid used during disinfecting and rinsing the system.

19. Disposable set for an extracorporeal blood treatment system, comprising:
an extracorporeal blood circuit comprising a blood withdrawal line and a blood return line configured to be coupled to a blood treatment device;
an infusion circuit comprising infusion lines coupled to the extracorporeal blood circuit;
an infusion valve unit configured to be releasably connected to an infusion pump of the extracorporeal blood treatment system, wherein the infusion valve unit comprises:
a body defining a valve seat having a platform attached to the body;
a first outlet and a second outlet attached to the body, wherein the first outlet is connected to one of the infusion lines and the second outlet is connected to a different infusion line of the infusion lines; and
a sealing element mounted to the platform, wherein the platform comprises a central opening and a fluid channel, wherein the sealing element comprises a stem extending through the central opening and a flexible structure extending radially from the stem and being configured to cover the fluid channel when the flexible structure is in a closed state;
wherein the sealing element allows infusion liquid to flow from an inlet of the infusion valve unit towards at least one of the first outlet and the second outlet and to block infusion liquid from flowing to the inlet from the first outlet and the second outlet.

20. The disposable set of claim 19, wherein the infusion lines comprise a pre-infusion line and a post-infusion line, the pre-infusion line connecting the infusion valve unit to the blood withdrawal line of the extracorporeal blood circuit and the post-infusion line connecting the infusion valve unit to the blood return line of the extracorporeal blood circuit.

21. The disposable set of claim 20, wherein the first outlet is coupled to the post-infusion line and the second outlet is coupled to the pre-infusion line.

22. The disposable set of claim 19, wherein the valve unit delimits an input chamber provided with the inlet and an output chamber provided with the first and second outlets, wherein the input chamber and the output chamber are separated from each other by a sealing mechanism.

23. The disposable set of claim 22, wherein the input chamber and the output chamber are cylindrical and reciprocally coaxial.

24. The disposable set of claim 22, wherein the first and the second outlets are orthogonal with respect to a main axis of the output chamber.

25. The disposable set of claim 22, wherein the inlet is aligned with respect to a main axis of the input chamber.

26. The disposable set of claim 22, wherein the output chamber is larger than the input chamber.

27. The disposable set of claim 19, wherein the infusion valve unit body is made of rigid material, the stiffness of the rigid material of the infusion valve unit body being such to support the infusion lines without deforming said valve unit.

28. The disposable set of claim 19, wherein the body of the infusion valve unit comprises a hollow cylinder that extends away from the platform and is open on a side opposite to the platform, the open side the cylinder comprising a flange, wherein the infusion valve unit further comprises a seal comprising an annular groove sized to receive a cylinder-shaped part of the valve unit and the flange.

29. Disposable set for an extracorporeal blood treatment system, comprising:
an extracorporeal blood circuit comprising a blood withdrawal line and a blood return line configured to be coupled to a blood treatment device;
an infusion circuit comprising infusion lines coupled to the extracorporeal blood circuit;
an infusion valve unit configured to be releasably connectable to an infusion pump of the extracorporeal blood treatment system wherein the infusion lines of the extracorporeal blood treatment system comprise a pre-infusion line and a post-infusion line, the pre-infusion line connecting the infusion valve unit to the blood withdrawal line of the extracorporeal blood circuit and the post-infusion line connecting the infusion valve unit to the blood return line of the extracorporeal blood circuit, wherein the infusion valve unit comprises:
a first outlet coupled to the post-infusion line and a second outlet coupled to the pre-infusion line;
a one-way valve configured to allow infusion liquid to flow from an inlet towards at least one of the first outlet and the second outlet and to block fluid flow towards the inlet:
an infusion valve unit body comprising the inlet and an input chamber in fluid communication with the inlet, the infusion valve unit body further comprising the first outlet and the second outlet and an output chamber in fluid communication with the first outlet and the second outlet,
wherein the input chamber and the output chamber are separated from each other within the infusion valve unit body by the one-way valve, wherein infusion fluid delivered into the input chamber through the inlet flows through the one-way valve directly into the output chamber within the infusion valve unit body.

30. The disposable set of claim 29, wherein the infusion valve unit body comprises a first part and a second part, wherein the second part comprises the first outlet and the second outlet and is configured to be releasably connectable to a first part of the infusion valve unit body, wherein said first part comprises the inlet and is mounted on a housing of the extracorporeal blood treatment system such that the inlet and the first chamber are configured to receive infusion liquid from the infusion pump.

31. The disposable set of claim 29, wherein the one-way valve comprises a valve seat and a sealing element mounted to the valve seat, wherein the valve seat has a central opening and at least one fluid channel, wherein the sealing element has a stem extending through the central opening and a flexible structure extending radially from the stem and being configured to cover the fluid channel when fluid pressure in the output chamber is greater than fluid pressure in input chamber.

32. The disposable set of claim 29, comprising an air trap inserted in the blood return line.

\* \* \* \* \*